United States Patent [19]

Lacour et al.

[11] Patent Number: 4,493,646
[45] Date of Patent: Jan. 15, 1985

[54] DEVICE FOR FIXING A TRANSMISSION ASSEMBLY IN THE BODY OF AN ANGLED DENTAL TOOL

[76] Inventors: Bernard Lacour, 16 Chemin de Brulefoin, 25000 Besancon; Hubert Euvrard, Chemin du Moulin, Auxon Dessus, 25870 Geneuille; Roger Gaillard, Busy, 25320 Montferrand le Chateau; Jean C. Boinot, 22 H, rue de Fontaine Ecu, 25000 Besancon, all of France

[21] Appl. No.: 401,611

[22] Filed: Jul. 26, 1982

[30] Foreign Application Priority Data

Aug. 3, 1981 [FR] France .................................. 81 15144
Dec. 1, 1981 [FR] France .................................. 81 22616

[51] Int. Cl.³ .............................................. A61C 1/12
[52] U.S. Cl. .................................................. 433/133
[58] Field of Search ................................ 433/133, 105

[56] References Cited

U.S. PATENT DOCUMENTS 1,678,096  7/1928  Andersen ........................... 433/130
3,475,817 11/1969  Loge .................................. 433/126

*Primary Examiner*—Robert Peshock
*Attorney, Agent, or Firm*—Robert E. Burns; Emmanuel J. Lobato; Bruce L. Adams

[57] ABSTRACT

A device for connecting to the body of a dentistry counter-angle the unit for transmitting the rotary movement of the major axis of the counter-angle to the oblique shaft contained in the head of the counter-angle. The transmission assembly is placed inside a socket (5), forming a case, the socket itself being fixed to the body of the counter-angle by means of a bayonet attachment, consisting of at least one pin (16), fixed to the inner wall of the body of the counter-angle, and of at least one L-shaped slot (12), formed on the socket. Application to the rapid assembling and dismantling of dentistry equipment.

1 Claim, 14 Drawing Figures

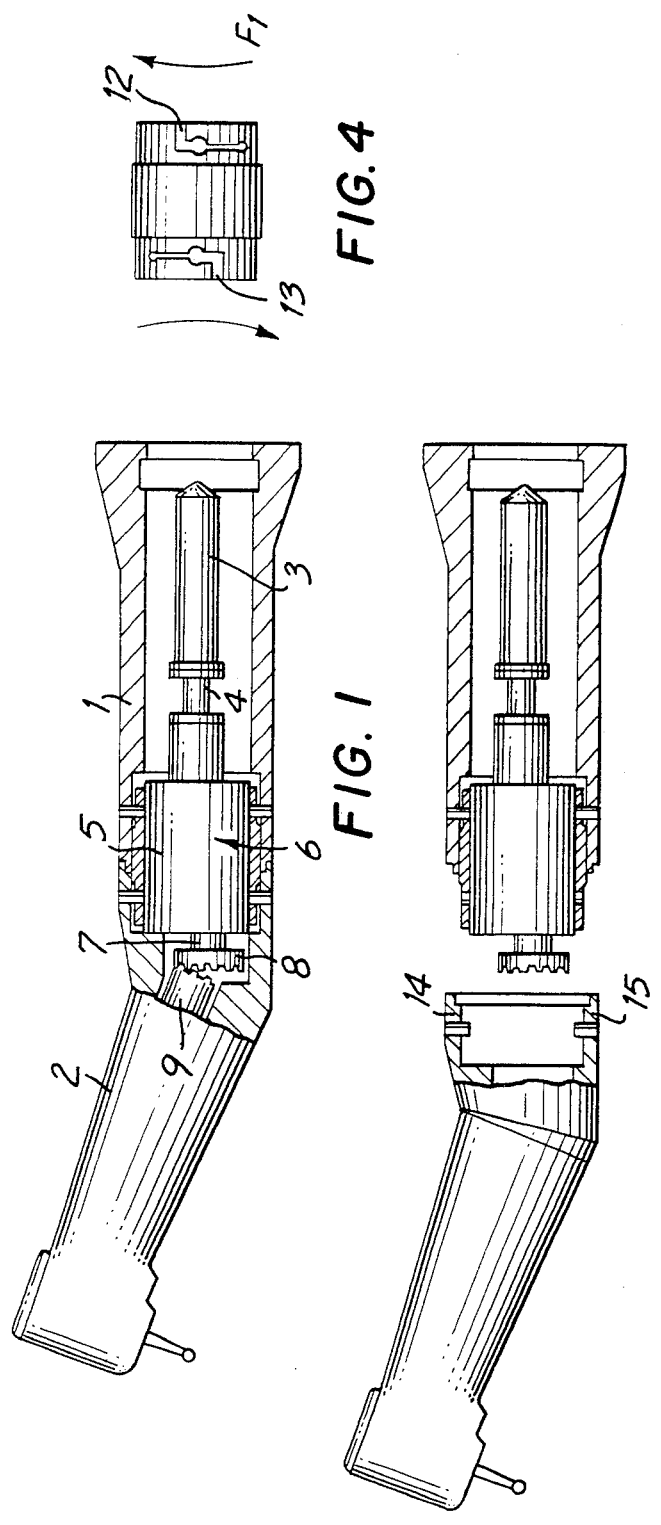
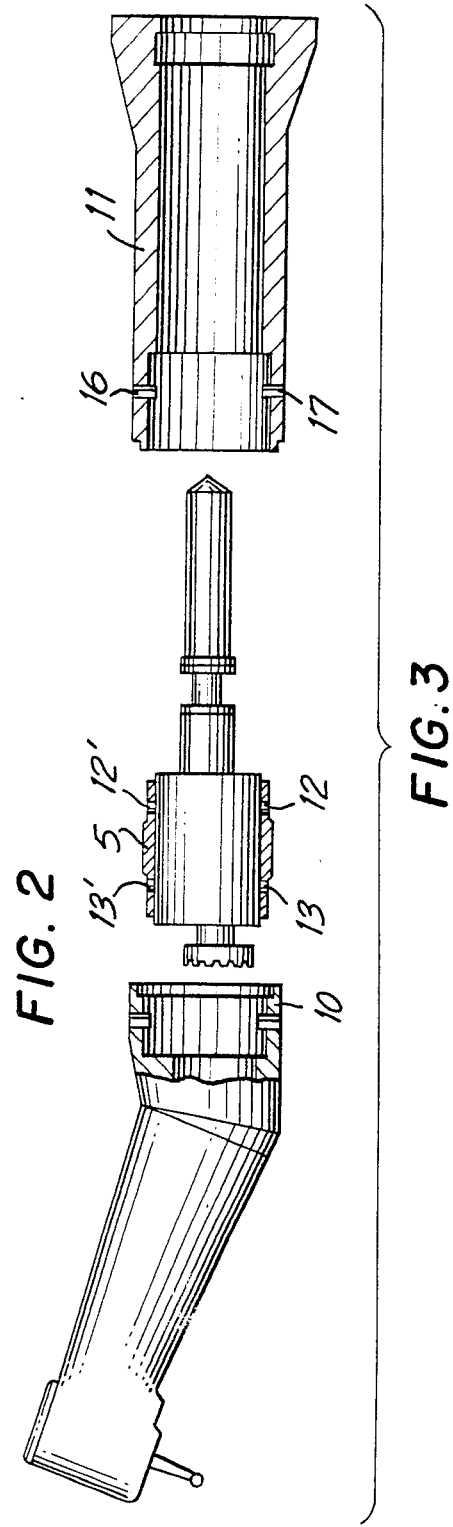

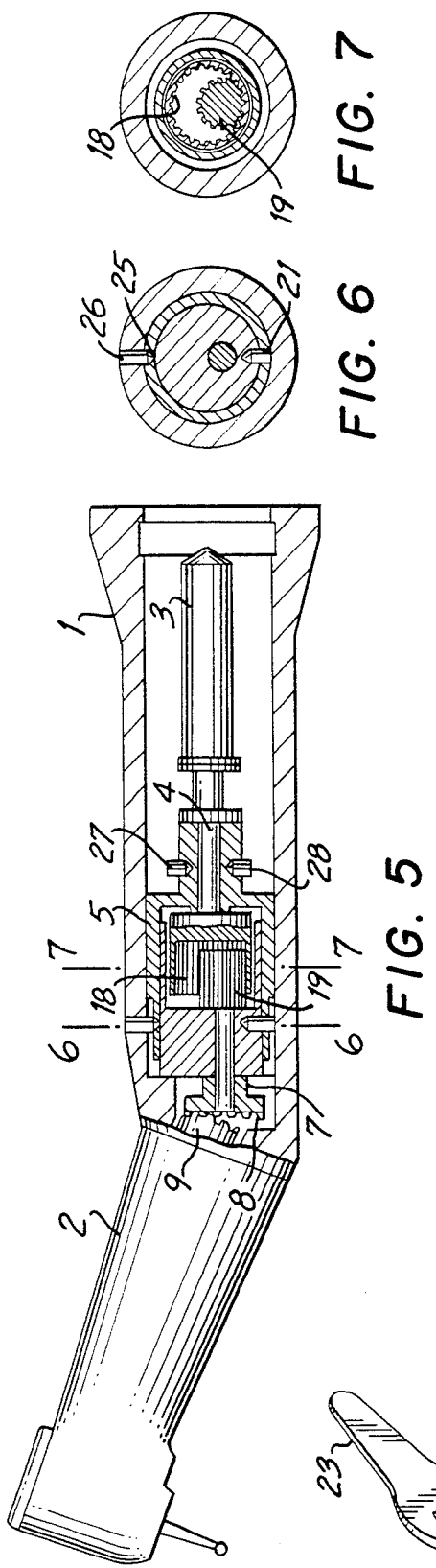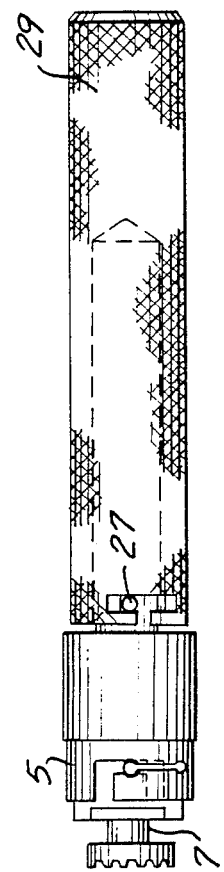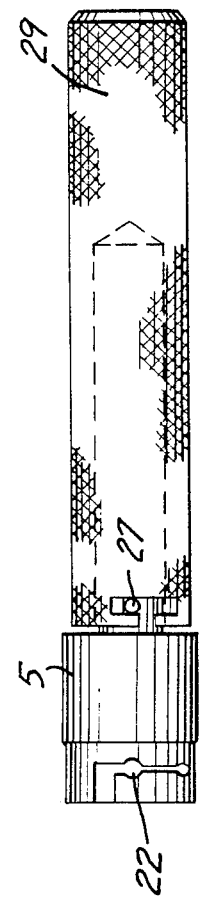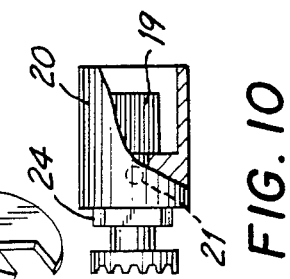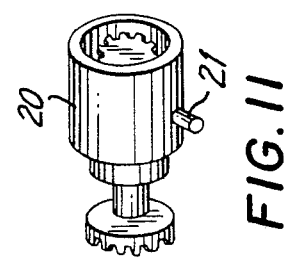

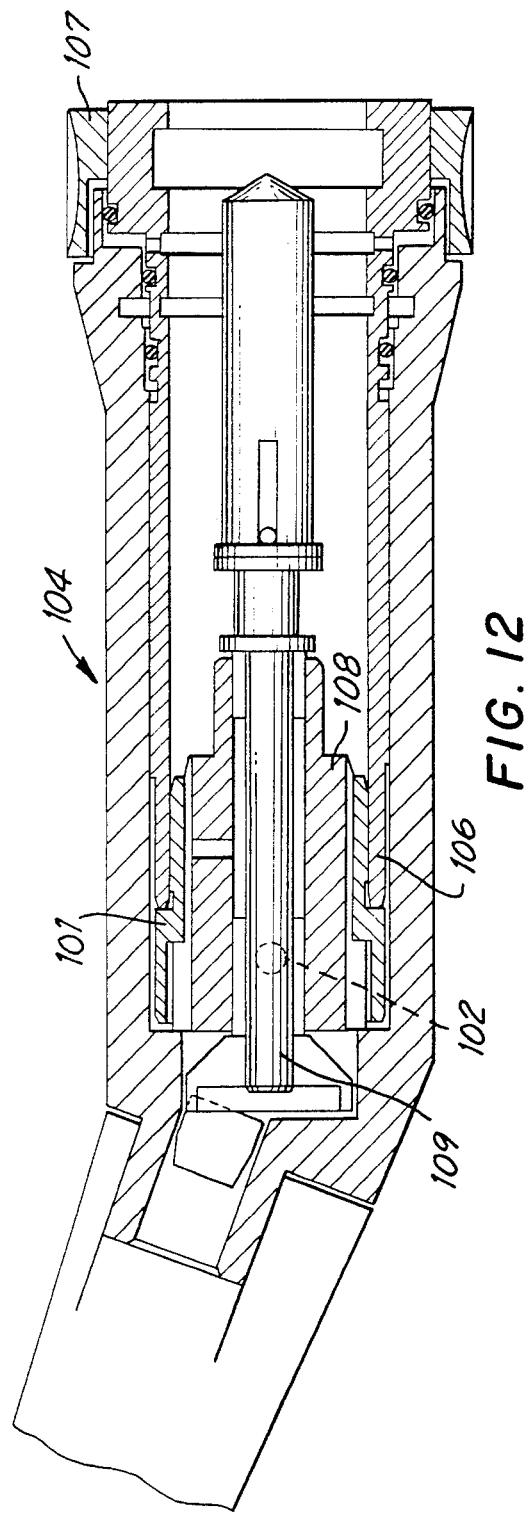
FIG. 12
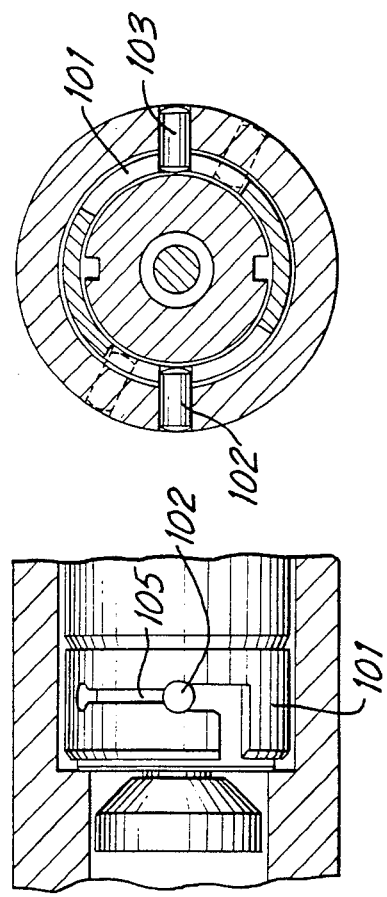
FIG. 14
FIG. 13

DEVICE FOR FIXING A TRANSMISSION ASSEMBLY IN THE BODY OF AN ANGLED DENTAL TOOL

BACKGROUND OF THE INVENTION

The subject of the present invention is a device for attaching or coupling to the body of a dentistry counter-angle the unit for transmitting with, reduction or step-up, if appropriate, the rotary movement of the major axis of the counter-angle to the oblique shaft contained in the head of the counter-angle and driving the tool carried by the rotating head.

Devices of this type are already known and have been described in numerous patent applications.

However, almost all of them have the shortcoming of requiring assembling and dismantling tools, but, above all, the relative positioning of the elements to be assembled is not reliably obtained. Thus certain devices make use of screwing and, due to the extent of screwing, the appropriate positioning is not obtained.

SUMMARY OF THE INVENTION

It is an object of the invention to overcome these shortcomings by a device, which makes possible a simple and effective attachment of a transmission assembly to the body of a dentistry counter-angle, without threading or fixed coupling. Furthermore, this device makes extremely rapid dismantling possible, for example with a view to cleaning or changing a defective or worn part. Finally, the coupling obtained is very rigid.

In accordance with the invention, this result is obtained with a device for removably coupling to the body of a dentistry counter-angle the unit for transmitting, with reduction or step-up, if appropriate, the rotary movement of the major axis of the counter-angle to the oblique shaft contained in the head of the counter-angle and driving the tool carried by the rotating head characterised in that the transmission assembly is placed inside a socket, forming a case, the socket being itself coupled to the body of the counter-angle by means of a bayonet attachment, consisting of at least one pin, fixed to the inner wall of the body of the counter-angle, and of at least one L-shaped slot, formed on the socket.

The transmission assembly includes a bearing permitting rotation of the major axis of the counter-angle (with or without step-up or reduction) and, according to a first embodiment, the bearing can be driven into the abovementioned socket.

In that case, the socket will contain at least one further L-shaped slot, opposite to the previous one, on the socket, enabling another part of the body of the counter-angle to be attached to the socket. This embodiment thus comprises a counter-angle in two parts, which are fixed to each other by the socket forming a case, in each instance, by means of at least one bayonet type device with L-shaped slot and pin on the inner face of the respective part of the body or the counter-angle.

According to a construction variant, the bearing can also be fixed in the socket, in which it is placed, by means of a bayonet coupling of the abovementioned type. In that case, it will be necessary to use tools for disengaging the elements, but their relative positioning will be accurate and the coupling obtained will be very rigid.

In this construction variant, the body of the manual part is made in one piece and the socket is fixed to said body of the manual part by means of a bayonet coupling as described above.

The invention will be understood more clearly with the aid of the description below of several embodiments in accordance with the invention, with reference to the attached drawings, in which:

FIG. 1 is a view in elevation, with partial section, of a first mode of application of the invention;

FIG. 2 is a view in elevation, with partial section, of the two elements of the counter-angle before being assembled;

FIG. 3 is a view in elevation, with partial section of the head, of the body of the counter-angle and of the transmission assembly before being assembled;

FIG. 4 is a view in elevation of the socket fixing the two parts of the body of the counter-angle;

FIG. 5 is a view in elevation, with partial section, of a second mode of application of the invention;

FIG. 6 is a section along second line A—A of FIG. 5;

FIG. 7 is a section along second line B—B of FIG. 5;

FIG. 8 represents a tool used for withdrawing the socket from the body of the counter-angle;

FIG. 9 represents a tool of FIG. 8 after the removal of the bearing;

FIG. 10 represents the bearing and a spanner for withdrawing it from the socket;

FIG. 11 is a view in perspective of the bearing and of its pin for fixing to the socket;

FIG. 12 is a view in longitudinal section of a third application variant of the invention;

FIG. 13 is a view from below of FIG. 12; and

FIG. 14 is a view, in transverse section, of FIG. 12 at the level of the pins and giving a diagrammatic representation of the locking mechanism.

Reference will be made, in the first place, to FIG. 1. A head (2) is fixed to the body (1) of the counter-angle with the aid of a bayonet attachment, similar to that described in Patent application No. 78-37,117 in the name of the Applicant. This device will not be described in greater detail and reference may be made to this document. It is clear, however, that provision of an attachment device of a known type, other than that of said application, would not go beyond the scope of the present application.

Placed in the body of the counter-angle is the drive (3), which is coupled, in a manner that is known per se, with the motor drive. The drive (3) drives a shaft (4), the end of which rotates in a box (5), adjusted to an easy fit in the body (1) of the counter-angle.

This case can be merely a simple bearing, in which the major axis of the counter-angle would rotate.

The shaft (4), via the transmission assembly (6), contained in the box (5), controls a shaft (7), which is supported by a bearing driven into the box (5), said shaft (7) having, at its end projecting from the box, a pinion (8) driving the shaft of the head via a pinion (9), fixed to the latter.

In the embodiment of FIGS. 1 to 4, the body of the counter-angle is composed of two parts, respectively the front part (10) and the rear part (11). The head of the counter-angle is directly connected to the front part (10).

The socket (5), in this case, acts as a joint between the two parts (10) and (11). For this purpose, it has, at each of its ends, two diametrically opposite bayonet type inlets (12, 12') and (13,13'), into which the corresponding pins (14) and (15) of the front part (10) and pins (16, 17) of the rear part (11) are inserted.

In order to disengage the two elements (10) and (11) of the body of the counter-angle, the rear part of the counter-angle is turned in the direction of the arrow F1 of FIG. 4, passing by two detaching hooks. The pin (17) of the body then reaches the longitudinal part of the L of the slot (12), while the pin (15) of the front part (10) enters the longitudinal part of the L of the slot (13). All that has to be done for completely dismantling the counter-angle is to separate the three parts from one another and disengage the head.

To disengage the two elements (10) and (11) of the body of the counter-angle, while keeping the box (5) fixed to the part (11), the rear part of the counter-angle is turned in the direction of the arrow F1 of FIG. 4 up to a first detaching hook. The pin (15) of the front part (10) enters the longitudinal part of the L of the slot (13). All that has to be done is to separate the two parts from each other.

The body (5) can also deal first with the dismantling of the pin (17), so as to keep the box (5) fixed to the part (10).

This embodiment does not necessitate the use of spanners.

The embodiment of FIGS. 5 to 11 will now be described.

In this embodiment, the socket (5) contains a pinion gear with a view to stepping up or reducing the speed of the motor for transmitting the rotation to the pinion (9) of the sloping arm of the head (2) of the counter-angle.

By way of example, a transmission has been described, in which a pinion (18), consisting of an interior dental crown, controls a driven pinion (19). The pinion (19) is fixed to the shaft (7), which rotates in a cylindrical bearing (20), (see FIG. 10). The bearing (20) is adjusted to an easy fit in the socket (5). It contains a pin (21), which is inserted into an L-shaped slot (22) of the socket (5), so as to produce, here again, a bayonet coupling.

In order to facilitate insertion and retraction of the bearing (20) and of the shaft, which it supports in the socket (5), a spanner (23) will be provided, enabling an effective grip to be established on an angular structure (24) of the bearing.

In order to fix the assembly consisting of the socket (5) and the bearing (20) into the body of the counter-angle, a second L-shaped slot (25), similar to the slot (13) of the first embodiment, is formed on said socket. This slot engages with a pin (26) of the body (1).

In order to facilitate the insertion or withdrawal of the socket (5) in its housing inside the body (1), the following have been provided:

two pins (27, 28), placed on the rear part of the socket; and a spanner (29).

The spanner (29) consists of a milled cylindrical body, hollowed so as to correspond in diameter to the rear end of the socket (5) and enabling the drive (3) to be inserted there. The spanner comprises a dual bayonet inlet, in which the pins (27) and (28) come to rest. It makes it possible to impart rotation to the socket (5) and then to withdraw it from the body of the counter-angle by releasing the pin (26) from the L-shaped slot (22). This spanner then makes it possible to hold the socket during the rotation imparted by the spanner (23) to the bearing (20).

Here again, any threading or fixed coupling is avoided.

In order to reach the same result and dispensing with the use of a spanner, it is possible to use the device shown in FIGS. 12 to 14.

The case (101) is fixed by means of at least one pin (102), preferably two pins (102, 103) with the body (104) of the counter-angle, said pins engaging with the L-shaped slots (105) of the case (101), so as to produce bayonet type closures.

The case (101) is fixed with a socket (106), sliding in a lubricated fit in the body (104) and ending behind the counter-angle in a collar (107), driven into, and/or stuck onto,, the rear part of said socket (106).

This collar (107) is accessible from the outside and can be turned by hand about the axis of the body of the counter-angle.

The case (101) is adjusted to a lubricated fit on the bearing (108), in which the shaft (109) of the counter-angle rotates.

In order to open the counter-angle, that is to say in order to withdraw the case (101), all that has to be done is to turn the collar (107) by about 30 degrees and then to pull the assembly, comprising the socket (106) and the bearing (108), out of the body. The bearing can then be withdrawn from the socket (106).

This device does not interfere, in any way, with the passage of the spray tubes in the case of internal spray counter-angles.

Besides, it makes it possible to dispense with the use of a dismantling tool.

In the embodiments described, fixing has been carried out by pins engaging with L-shaped slots. These slots are of the type of those described in French Patent Application Nos. 77-04,027 and 78-37,117 in the name of the Applicant.

It is essential to note that the bayonet fittings that can be used have a very specific structure and shape. The effect of this shape is not only firmly to fix the two parts which it unites, but its effect is also to draw these parts together. This traction effect can be more or less enhanced by slightly offsetting the pins, which interlock in the slots of the bayonet fitting; the latter, by virtue of its cut, can be slightly deformed and supported in the desired direction.

We claim:

1. A contra angle combination comprising, a contra angle head having a driven spindle for driving a rotary-driven dental tool mounted on the head, said spindle having a driven pinion gear rigidly fixed thereto on an end of said spindle for receiving driving input thereto to rotate said spindle, a drive transmission assembly having a driving shaft with an end pinion gear rigidly fixed thereto for meshing only with several teeth thereof with some teeth of the first-mentioned pinion gear, when the transmission assembly is coupled to the contra angle head and is at rest, the axes of rotation of said first-mentioned gear being at an oblique angle so that only partial meshing occurs when said drive transmission assembly is coupled to said contra angle head, and is at rest, an elongated housing having a socket for receiving and housing the drive transmission assembly, a bayonet coupling releasably holding the drive transmission assembly in said socket of said housing, a second bayonet coupling for detachably coupling said housing to said contra angle head, said drive transmission shaft having an externally toothed element at an opposite end to the pinion gear thereon, an internally toothed element fitting over and circumferentially of the externally toothed element for detachably coupling thereto, and another shaft fixed to said internally toothed element and extending axially therefrom for driving the internally toothed element thereby to drive the pinion gear connected to said drive transmission, whereby the pinion gears can be driven at speeds only partially dependent on the gear ratio between the pinion gears.

* * * * *